(12) United States Patent
Tupin, Jr.

(10) Patent No.: US 10,398,342 B2
(45) Date of Patent: Sep. 3, 2019

(54) IMPEDANCE MATCHING TRANSFORMER FOR COUPLING ULTRA WIDEBAND (UWB) RADAR TRANSCEIVER TO A HUMAN BODY

(71) Applicant: Joe P. Tupin, Jr., Truckee, CA (US)

(72) Inventor: Joe P. Tupin, Jr., Truckee, CA (US)

(73) Assignee: Lifewave Biomedical, Inc., Los Altos, CA (US)

( * ) Notice: Subject to any disclaimer, the term of this patent is extended or adjusted under 35 U.S.C. 154(b) by 0 days.

(21) Appl. No.: 15/582,171

(22) Filed: Apr. 28, 2017

(65) Prior Publication Data

US 2017/0325706 A1 Nov. 16, 2017

Related U.S. Application Data

(63) Continuation of application No. 14/715,502, filed on May 18, 2015, now abandoned, which is a
(Continued)

(51) Int. Cl.
*A61B 5/00* (2006.01)
*A61B 5/05* (2006.01)
(Continued)

(52) U.S. Cl.
CPC .............. *A61B 5/05* (2013.01); *A61B 5/0002* (2013.01); *A61B 5/6892* (2013.01); *G01S 7/28* (2013.01);
(Continued)

(58) Field of Classification Search
CPC ........ A61B 5/05; A61B 5/0002; A61B 5/6892; A61B 5/0205; A61B 2503/045;
(Continued)

(56) References Cited

U.S. PATENT DOCUMENTS 5,315,995 A 5/1994 Rivers
5,853,005 A * 12/1998 Scanlon ................. A61B 5/113
600/459

(Continued)

OTHER PUBLICATIONS

Dissanayake et al., UWB Antenna Impedance Matching in Biomedical Implants, Antennas and Propagation, EuCAP 2009, pp. 3523-3526.*

(Continued)

*Primary Examiner* — Jacqueline Cheng
*Assistant Examiner* — Tho Q Tran
(74) *Attorney, Agent, or Firm* — Haverstock & Owens LLP (57) ABSTRACT

Ultra wideband patient monitoring systems, and particularly baby monitoring systems, adapted to prevent reflective loss between the antenna and the patient's body. The devices, systems and methods described herein may be used to efficiently couple UWB energy to a patient for patient monitoring. In particular, described herein are impedance transformer pads, mats and the like, upon which a patient may comfortably lie while being monitored via one or more UWB sensors (e.g., antenna); the impedance transformer pads help match the impedance and prevent reflective loss of UWB energy. Also described herein are bassinets, including NICU bassinets and baby monitors.

19 Claims, 5 Drawing Sheets

Related U.S. Application Data continuation of application No. 13/196,139, filed on Aug. 2, 2011, now abandoned.

(60) Provisional application No. 61/369,843, filed on Aug. 2, 2010.

(51) Int. Cl.
| | | |
|---|---|---|
| *H01Q 5/25* | (2015.01) | |
| *G01S 13/02* | (2006.01) | |
| *G01S 13/88* | (2006.01) | |
| *G01S 7/28* | (2006.01) | |
| *G01S 13/42* | (2006.01) | |
| *A61B 5/0205* | (2006.01) | |

(52) U.S. Cl.
CPC .......... *G01S 13/0209* (2013.01); *G01S 13/42* (2013.01); *G01S 13/88* (2013.01); *H01Q 5/25* (2015.01); *A61B 5/0205* (2013.01); *A61B 2503/045* (2013.01)

(58) Field of Classification Search
CPC . G01S 13/88; G01S 13/42; G01S 7/28; G01S 13/0209; H01Q 5/25
USPC .......................................................... 600/481
See application file for complete search history.

(56) References Cited

U.S. PATENT DOCUMENTS

| | | | |
|---|---|---|---|
| 9,002,427 B2 | 7/2015 | Tupin, Jr. | |
| 2002/0140215 A1* | 10/2002 | Breed | B60N 2/853 |
| | | | 280/735 |
| 2002/0156379 A1* | 10/2002 | Angelsen | B06B 1/0614 |
| | | | 600/459 |
| 2004/0249257 A1 | 12/2004 | Tupin, Jr. | |
| 2005/0052322 A1 | 3/2005 | Park | |
| 2006/0058681 A1* | 3/2006 | Eberle | A61B 8/06 |
| | | | 600/466 |
| 2006/0111642 A1 | 5/2006 | Baura | |
| 2006/0287600 A1 | 12/2006 | McEowen | |
| 2008/0001735 A1 | 1/2008 | Tran | |
| 2008/0015439 A1 | 1/2008 | Raju | |
| 2008/0252293 A1 | 10/2008 | Lagae | |
| 2008/0294019 A1 | 11/2008 | Tran | |
| 2009/0227882 A1* | 9/2009 | Foo | A61B 5/0205 |
| | | | 600/508 |
| 2009/0238426 A1 | 9/2009 | Fear | |
| 2010/0152600 A1 | 6/2010 | Droitcour | |
| 2011/0112423 A1 | 5/2011 | Champman | |

OTHER PUBLICATIONS

Staderini, UWB Radars in Medicine, Jan. 2002, IEEE AESS Systems Magazine, pp. 13-18.

\* cited by examiner

IMPEDANCE MATCHING TRANSFORMER FOR COUPLING ULTRA WIDEBAND (UWB) RADAR TRANSCEIVER TO A HUMAN BODY

CROSS REFERENCE TO RELATED APPLICATIONS

This patent application is a continuation of U.S. patent application Ser. No. 14/715,502, filed May 18, 2015, titled "ULTRA WIDEBAND (UWB) BABY MONITORS FOR DETECTION OF INFANT CARDIOPULMONARY DISTRESS", which is a continuation of U.S. patent application Ser. No. 13/196,139, filed Aug. 2, 2011, titled "ULTRA WIDEBAND (UWB) BABY MONITORS FOR DETECTION OF INFANT CARDIOPULMONARY DISTRESS," Publication No. US-2012-0059268-A1, which claims priority to U.S. Provisional Patent Application No. 61/369,843, titled "NON-CONTACT BABY MONITOR FOR THE NEONATAL INTENSIVE CARE UNIT WITH APPLICATION TO HOME MONITORING FOR DETECTION OF CARDIOPULMONARY DISTRESS" filed on Aug. 2, 2010, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are non-contact baby monitors for monitoring an infant. In particular, described herein are ultra wideband (UWB) baby monitoring systems for measuring an infant's cardiopulmonary state, and detecting distress. Included herein are devices including integrated UWB monitors and bassinettes and/or impedance transformer pads for optimizing the transfer of energy between the UWB system and the infant being monitored.

BACKGROUND

The Neonatal Intensive Care Unit (NICU) is a unit of a hospital specializing in the care of ill or premature newborn infants. Approximately 500,000 babies born in the United States each year are treated in a neonatal intensive care unit with the most common causes for admission being premature birth, difficult delivery, breathing problems, infections, and birth defects.

NICU protocols specify continuous monitoring of vital signs, to alert caregivers of a deteriorating condition or an emergent event. These events can develop slowly, as in hyperkalemia, which can lead to cardiac arrhythmia, or can appear suddenly, as commonly seen in respiratory distress. Current monitoring techniques rely heavily on ECG technology which requires direct skin contact via adhesive electrodes and are thus highly undesirable due to the need for skin contact. Premature babies have extremely delicate skin that is susceptible to damage and infection, increasing their risk of complications and potentially extending their time in the NICU. Premature babies younger than 30 to 32 weeks have thin skin, lacking the layers of body fat that would have been put on during the final weeks of pregnancy. In extremely premature babies, the coarse, top layer of skin hasn't yet formed. During their stay in the NICU, every attempt is made to minimize skin contact, even limiting physical contact by parents and caregivers.

Besides the potential for complications resulting from direct placement of electrodes on the infant's skin, there is an identified need to reduce the amount of physical contact to the neonatal intensive care patient since contact is known to stress the infant and can compromise recovery and development. Thus, monitoring technologies that minimize placement of electrodes on the patient as well as minimize the need for caregivers to touch the patient to collect vital signs information are highly desirable.

Thus, there is a need for non-contact baby/infant monitors, and this need is particularly acute in the NICU context. A number of variations of non-contact UWB sensors have been proposed, such as those offered by Sensiotec, and described in U.S. Pat. No. 7,432,847 and U.S. 2009/0227882. However, these devices suffer from limitations inherent in their configuration resulting in a loss of signal strength. This loss of signal strength results in less efficient devices, and may limit the penetration and accuracy. Thus, it would be useful to provide systems, devices and methods for monitoring an infant, and particularly an infant in an NICU setting in a reliable, low-energy and non-contact fashion. Described herein are systems, devices and methods that may address this need.

SUMMARY OF THE DISCLOSURE

Described herein are non-contact monitoring UWB systems, which may also be referred to as UWB radar systems or UWB radar monitoring systems. In particular, described herein are UWB monitoring systems that provide impedance matching between the emitter (and/or receiver) antenna and the patient such that the emitted UWB energy is efficiently transmitted and received. In some variations the system may include an impedance transformer, configured as a pad or other reclining surface that matches the impedance (e.g., dielectric) of the antenna to that of the patient. The impedance transformer may thereby reduce the reflection of UWB energy between the antenna and the patient, preventing energy loss and allowing more efficient operation. In some variations, the system includes a dedicated bassinet in which the UWB components have been integrated; integration may allow optimization of the positioning of the UWB antenna. Also described herein are systems configured to be used with existing cribs or basinets for monitoring (including at-home monitoring).

For example, described herein are impedance transformer pads for use with an ultra wideband (UWB) monitoring system to minimize reflective loss of the UWB energy. The impedance transformer pads may include: a soft or resilient recumbent surface formed at least in part from an impedance transformer region having a thickness of between about 0.4 cm and 7 cm, wherein the impedance transformer region has at least one layer having a dielectric constant of between about 5 and about 20; and a UWB antenna abutting the impedance transformer region; wherein the UWB antenna is configured to transmit and receive UWB signals through the impedance transformer region to monitor the patient resting on the pad.

Any of the 1, wherein the pads described herein may be for use with (or integrated into) a bassinet. For example, the recumbent surface may be sized to fit into a bassinet.

In some variations the impedance transformer region has a single homogenous layer. This layer may have a dielectric value that is intermediate between the dielectric constant of the UWB antenna(s) and the patient (e.g., the geometric mean). Impedance transformer regions may include multiple layers (e.g., 2, 3, 4, 5, 6, etc.); virtually any number of layers may be included, however, this may increase the cost and complexity of the devices. In some variations, the impedance transformer region has at least two adjacent planar layers, wherein each planar layer has a different thickness and dielectric constant. For example, in some variations, the impedance transformer region has three adjacent planar layers, wherein each planar layer has a different thickness and dielectric constant.

The impedance transformer region (including each layer thereof) may be formed of any appropriate material that may take the desired thickness and dielectric properties, as well as being biocompatible, pliable/soft, easy to clean, non-toxic, hypoallergenic, and water proof. For example in some variations the layer(s) of the impedance transformer region are formed of silicone.

The size of the impedance transformer region may have a thickness of between about 0.5 cm and 5 cm, including all of the layers, if more than one layer is present.

In some variation, the pad includes a backing layer beneath the impedance transformer region and the UWB antenna. The pad may include a plurality of UWB antennas beneath and abutting the impedance transformer region. The antenna may be configured to emit a UWB signal having a bandwidth, and wherein the impedance transformer region has one or more planar layers each having a dielectric and wherein and the thickness of each layer is approximately one quarter or one half of the wavelength of the center frequency of the bandwidth in the dielectric of that layer.

Also described herein are ultra wideband (UWB) patient monitoring systems having an impedance transformer pad to minimize reflective loss, the system having a UWB bandwidth for emitting sensing signals, the system further comprising: an impedance transformer pad having a UWB antenna beneath an impedance transformer region, the antenna configured to transmit UWB signals through the impedance transformer region to a patient resting on the pad, wherein the impedance transformer region has one or more planar layers and the thickness of each layer is approximately one quarter or one half of the wavelength of the center frequency of the bandwidth in the dielectric of that layer; and a processor configured to receive signals from the UWB antenna to monitor the patient. Any of the systems and devices described herein may also include UWB electronics (which may be separate from or incorporated into a processor) for generating a UWB signal for transmission and reception by the UWB antenna. Such UWB electronics may include signal generators, D/A and A/D converters, timing circuitry, comparators, amplifiers, filters, and the like. For example see U.S. Pat. No. 7,725,150, U.S. patent application Ser. No. 12/765,680, published as US 2010/0274145A1, and U.S. patent application Ser. No. 12/749,861, published as US 2011/0060215A1. The UWB electronics are typically configured to generate the UWB signal(s) for emitting from the antenna(s) and processing the received signal (reflections) to extract physiological data.

As mentioned, the impedance transformer pad may also include a backing layer behind the impedance transformer layer and the antenna. The backing layer may support the recumbent surface formed by the impedance transfer region (or it may form the recumbent surface with the impedance transfer region).

In some variations the pad includes a cable connecting the antenna of the impedance transformer pad to the UWB electronics and/or processor.

In general, the impedance transformer pad is flexible, hypoallergenic, and water proof. The pad may be used with a crib or bassinet. For example, the pad may be sized for use in a crib or bassinet, including a NICU. In some variation the pad includes indicators (e.g., markings) indicating the location of the sensors/antenna and/or the preferred positioning for the patient (e.g., infant) lying upon the pad.

In some variations the impedance transformer region of the impedance transformer pad has a single homogenous layer configured as a quarter wavelength layer, wherein the thickness is approximately one quarter of the wavelength of the center frequency of the bandwidth in the dielectric of the layer. In some variations the impedance transformer region of the impedance transformer pad has two or more layers.

In some variations, the impedance transformer region of the impedance transformer pad has three layers, comprising adjacent planar layers configured as a quarter wavelength layer, a half wavelength layer, and a quarter wavelength layer.

In any of the variations described herein, the impedance transformer pad may include a plurality of UWB antennas. Different antenna may be used, or the same types of antenna. For example, the UWB antenna may be an air antenna (e.g., an antenna readily commercially available that is configured for transmission in air, and therefore is designed to transfer energy into a medium with a relative dielectric constant of approximately 1).

Also described herein are methods of monitoring an infant using an ultra wideband (UWB) radar system including an impedance transformer pad, the method comprising: placing the infant atop the impedance transformer pad; and emitting a UWB signal from a UWB antenna, wherein the signal passes from the antenna, through an impedance transformer region of the impedance transformer pad and into the infant, further wherein the impedance transformer region has at least one layer having a dielectric constant of between about 5 and about 20, wherein the impedance transformer pad reduces the impedance miss-match between the antenna and the infant to reduce reflective loss of energy from the signal.

The method may also include receiving a reflected UWB signal from the infant using the UWB antenna, and analyzing the signal to monitor the infant. The method may include determining a vital sign for the infant and in some variations, displaying the vital sign. For example, the signal may be analyzed to determine heart rate, etc. The system may include one or more alarms for indicating when the infant is undergoing distress based on the monitoring. In general, the systems, methods and devices described herein may use one or more antennas that can be configured as emitter antenna (transmitting the UWB signal) and/or receiver antenna (receiving the UWB signal reflected), or both. Thus, a recovering antenna can be the same as the transmitting antenna.

The step of emitting the UWB signal may include passing the signal through the impedance transformer region wherein the impedance transformer region has a single homogenous planar layer having a dielectric that is the geometric mean of the dielectric of the antenna and the dielectric of the infant. In some variations, emitting the UWB signal comprises passing the signal through the impedance transformer region wherein the impedance transformer region has a thickness between about 0.4 cm and about 7 cm.

The step of emitting the UWB signal may include passing the signal through the impedance transformer region wherein the impedance transformer region has a plurality of layers each with a dielectric value, wherein the thickness of each layer is approximately one quarter or one half of the wavelength of a center frequency of the bandwidth of the emitted signal in the dielectric of that layer. In general the step of emitting comprises emitting the UWB signal from the antenna to the infant through the impedance transformer region without the UWB passing thought the air or a standard mattress (which may result in increased loss when the impedance transfer pads described herein).

In any of the method described herein, placing the infant on the pad may comprise placing the infant atop the impedance transformer pad within an NICU bassinet.

Also described herein are ultra wideband (UWB) baby monitoring systems including: an impedance transformer pad having a soft or resilient recumbent surface upon which a baby may rest; a UWB antenna coupled to the impedance transformer pad and configured to emit a UWB signal through the transformer pad and into the baby, wherein the impedance transformer pad is configured to prevent reflective loss of more than 50% of energy of the UWB signal; and a processor in communication with the UWB antenna and configured to monitor the baby when the baby is resting on the impedance transformer pad. As mentioned, any of the systems and devices described herein may also include UWB electronics as part of (or in addition to) the processor.

The system may generally be configured to apply UWB signals in a bandwidth having a center frequency, wherein the impedance transformer pad comprises an impedance transformer region forming the recumbent surface, the impedance transformer region having one or more planar layers each with a different dielectric value. For example, the system may be configured to apply UWB signals in a bandwidth having a center frequency, wherein the impedance transformer pad comprises an impedance transformer region forming the recumbent surface, the impedance transformer region having one or more planar layers each with a dielectric value, wherein the thickness of each layer is less than or equal to one half of the wavelength of the center frequency in the dielectric of that layer. Specifically, the system may be configured to apply UWB signals in a bandwidth having a center frequency, wherein the impedance transformer pad comprises an impedance transformer region forming the recumbent surface, the impedance transformer region having one or more planar layers each with a dielectric value, wherein the thickness of each layer is approximately one quarter or one half of the wavelength of the center frequency in the dielectric of that layer.

As mentioned above, the impedance transformer pad may be configured to fit within a bassinet. Further, the impedance transformer pad may be made of a non-toxic, hypoallergenic, and water proof material.

Also described herein are bassinets configured for ultra wideband (UWB) monitoring of an infant. For example, the bassinet may include: a temperature-regulated bassinet enclosure having walls and a lower surface; and at least one UWB antenna integrated into the bassinet and configured to emit UWB energy into an infant within the bassinet from the lower surface of the bassinet; wherein the lower surface of the bassinet impedance matches to minimize reflective loss of UWB energy between the UWB antenna and the infant.

In some variations, the lower surface of the bassinet comprises an impedance transformer pad covering the UWB antenna so that the UWB antenna emits UWB signals through the impedance transformer pad. Any of the pads described above may be used; in some variations the pad is integrated into the bassinet.

The UWB antenna may be configured to apply UWB signals in a bandwidth having a center frequency, further wherein the lower surface comprises an impedance transformer region covering the UWB antenna, on which an infant may rest, wherein the impedance transformer region has one or more planar layers each with a dielectric value, wherein the thickness of each layer is less than one half of the wavelength of the center frequency in the dielectric of that layer.

In some variations, the UWB antenna may have a dielectric approximately matched to the dielectric of the infant. For example, the antenna may be configured to have an dielectric of approximately 50. The outer surface of the dielectric may be adapted so that it is comfortably for the infant to rest on top of. For example, the upper surface of the antenna may be soft, compliant, etc. In any of the variation described herein, the bassinet may include a plurality of UWB antennas. Further, the bassinet may include a processor (e.g., a UWB radar processor) configured to receive signals from the UWB antenna to monitor the infant, and/or UWB electronics for emitting and receiving UWB signals and extracting physiological data.

DETAILED DESCRIPTION

The Ultra-Wideband (UWB) monitoring systems described herein may also be referred to as medical radar systems. These systems allow for miniature, extremely low-power medical monitoring systems that are safe and effective. UWB medical radar is an active imaging technology similar in functional concept to ultrasound but is based on electromagnetic, rather than sonic energy. In practice, the systems described herein emit a micro-pulse of electromagnetic energy, typically on the order of one hundred picoseconds in duration, which propagates into the human body. As the energy enters the body, small amounts of the incident energy are reflected back to the device. The reflections are primarily a result of the differences in dielectric properties of the underlying tissues and organs, and can be detected as signals ("reflection signal energy"). The reflection signal energy is then received and processed using signal processing algorithms to extract information on the location, size, and relative movement of the illuminated tissues and organs. The short pulse duration also allows the radar to 'see' at much closer distances and with finer resolution than more traditional radar systems. The energy transmitted to the patient is typically reduced by unwanted reflections arising between the UWB antenna and the patient's body ("reflection loss"). The one-way reflection loss in some prior art UWB systems may be as great as 85-90% of the emitted energy. This loss results in lower signal strength overall, and a significant decrease in the reflected energy from the internal anatomical structures, making extraction of the desired physiological data more difficult and less accurate and reliable.

Thus, the systems described herein describe systems for reducing the reflection loss of the UWB sensor system. All of the UWB systems described herein employ extremely low power electromagnetic energy capable of passing through materials such as plastics, clothing, air and bone without needing direct skin contact, conductive gels, electrodes or leads. The actual transmitted power levels are well below thresholds set for governmental safety standards, as well as below those used by widely-adopted commercial wireless technology (e.g. cell phones, Bluetooth devices, ZigBee devices, 2.4/5.8 GHz cordless phone, wireless intercoms and baby monitors, and 802.11 wireless internet equipment).

The infant in the NICU environment provides some unique challenges and opportunities for non-invasive vital signs monitoring. First, the NICU infant is typically a premature baby and, thus the anatomical structures are very small, complicating the ability to collect vital signs data using non-contact active techniques. Second, a baby admitted to a NICU stays in a specialized isolation bassinette which provides a protective environment for the infant. The bassinette is typically an enclosed structure, controlling temperature, light, humidity, and air flow. They feature transparent sides that are typically made from clear plastic. The tops are removable—either manually or motorized, and often includes a switch that is used to signal when the top is open or closed.

In some variations of the devices described herein, the system includes a UWB medical radar to interrogate the volume of the isolation bassinette, allowing non-contact monitoring of vital signs including cardiac and respiratory activity, without touching the infant. These bassinettes are typically made using transparent plastic enclosure and a mattress pad—both of which are non-conductive; UWB radar can operate through the walls or the pad.

UWB Sensor Attached to Bassinet

In some variations, the systems described herein include bassinets with integrated UWB monitoring systems. In this variations, the UWB monitoring system and bassinet may be configured together to optimize the signal transmission and detection and therefore the efficiency of the monitoring system. For example, the UWB antenna(s) may be arranged (and may be fixed in positions) around the bassinet in a manner that optimizes the detection of infant vital signs. In some variations the bassinet may include one or more indicators for positioning the infant within the bassinet in a manner that provides optimal monitoring. In addition, the bottom of the bassinet may include a recumbent surface that is configured to optimize the transmission of UWB energy for sensing an infant. The UWB system may also be configured to sense the presence/absence of an infant in the bassinet, and to automatically monitor or turn off monitoring, and to emit or provide various alerts based on the condition of the infant.

Figure 1:
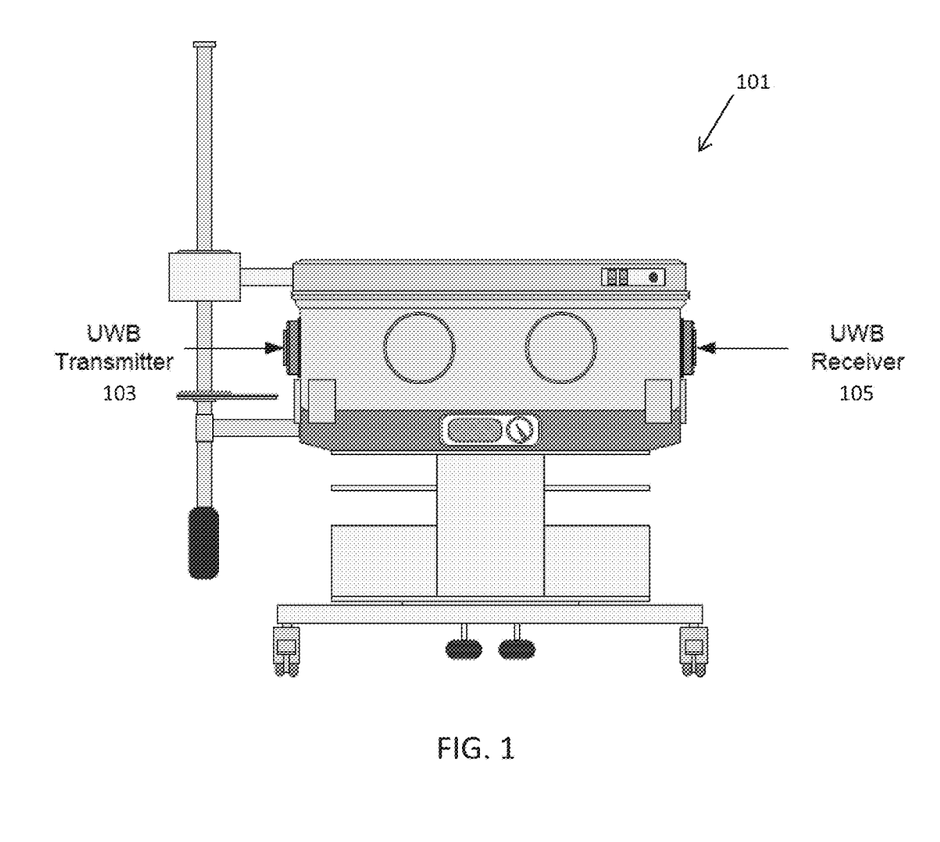
FIG. 1 shows one variation of an NICU bassinet with one variation of a UWB monitoring system.

For example, FIG. 1 shows one variation of a bassinette enclosure 101 in which one or more radar components (e.g., transmitter 103, receiver 105, or transceiver) on the walls of the isolation bassinette allow off-body detection and monitoring of cardiac and respiratory activity. In FIG. 1, the NICU bassinet includes a UWB sensor configured in a bistatic mode, with transmission 103 at one end and reception 105 at the other end of the enclosure 101). Thus, in general, the system architecture could include monostatic, bistatic, or multistatic topologies with locations including bassinette corners, sides, top, bottom, front or rear surfaces.

In one implementation, the components would be secured to the exterior surfaces to minimize the potential of any physical interaction with the infant. However, in some variations it may be advantageous to mount the radar components inside the bassinette—e.g. one or more corners, to provide a wider search area. The integrated cover switch can be used to disable the radar when the top cover is open.

In some variations, the system includes a plurality of UWB transmitter/receivers positioned in predetermined locations within the bassinet. The transmitter, receiver or transceiver may be arranged in a variety of configurations. In one variation, the UWB components are located in an interior corner (e.g., co-located transmitter and receiver operated in monostatic mode). Alternatively the UWB components may be located in any two opposite interior corners with separate transmitter and receiver operated in bistatic mode. In some variations, the UWB components are located on the exterior short side of the bassinet with a co-located transmitter and receiver operated in monostatic mode. In some variations the UWB components are located in opposite exterior short sides with separate transmitters and receivers operated in bistatic mode. In some variations, UWB components are located on an exterior long side with co-located transmitter and receiver operated in monostatic mode. Alternatively, the UWB components may be located on opposite exterior long sides with separate transmitters and receivers operated in bistatic mode. In some variations the UWB components may be operated on adjacent exterior long sides with separate transmitters and receivers operated in bistatic mode. In general, combination of three or more adjacent exterior long sides with separate transmitter and receiver may be operated in multistatic mode.

In addition to the variations just described, the bassinet may be configured so that UWB components (e.g., transmitter, receiver, or transceiver) form part of or are coupled to a recumbent surface (such as the bottom of the bassinet or a pad for the bottom of the bassinet) which may be impedance matched as described herein. This may further enhance the UWB signal transmission/reception and therefore the reliability and operation of the monitor. If impedance matching as described herein is not performed, a substantial amount of energy may be lost between the UWB antenna and the boundary of the infant's body (as much as 85-90%), resulting in a substantial decrease in efficiency and a loss of reflected energy from internal anatomic structures, making extraction of desired physiological data more difficult, less accurate and less reliable.

In general, a plurality of UWB transmitter, receivers and/or transceivers may be used. These elements may be multiplexed or used as part of a phased array. Examples of arrangements of phased arrays of UWB antenna are illustrated in US 2003/0090407 (specific to the use of such arrays for imaging).

In some variations the recumbent surface (e.g., bottom of the bassinet onto which the infant is directly placed) is flush with the outer surface of the one or more UWB antenna (transmitter, receiver and/or transceiver), even without an intermediate impedance transformer pad, such as those described below. In such cases the outer surface of the antenna is specifically configured (1) so that the infant may be placed directly atop it without discomfort or risk of damage to the infant or the antenna (e.g., it may be formed of a soft or resilient material), and the antenna itself may be adapted to have a dielectric value approximating the dielectric value of the infant's body (e.g., approximately 50).

One advantage of operating a UWB sensor(s) in an isolation bassinette is that the structure of the bassinet is physically bounded on all sides. The bassinet represents a constrained volume, and thus there is a finite range where the target—the infant, can be located in the bassinette. The system may be calibrated during installation or prior to placement of the infant in the bassinette to optimize the radar range and characterize the empty bassinette. This calibration data could then be used to create a filter that represents the empty bassinette. Once the infant is placed in the bassinette the filter would operate on the radar returns, producing an optimized signal that enhances the presence and motion of the infant, minimizing the potential for detection of false positives.

Impedance Transformer Pad with Integrated UWB Sensor

Any of the systems described herein may include a recumbent surface with integrated UWB components that is configured to match and/or optimize the impedances between the UWB antenna and the infant, and thereby substantially reduce reflection loss. In general, the recumbent surface may be a pad, table, platform, mattress, cushion, blanket, or the like, on which the infant is configured to lie, sit, or recline, where the recumbent surface acts as an interface between the UWB antenna and also acts as an impedance transformer to minimize reflection and improve energy transfer between the antenna and the infant.

For example, the sleeping pad in a NICU bassinette may be adapted to be (or include) an impedance transformer pad coupled to the UWB antenna(s) for monitoring the infant. NICU bassinette pads are typically made of high density foam rubber with a vinyl coating and are primarily designed for comfort. Such foamed pads are typically very lossy, at least in part because of the presence of air pockets within the foamed material, so that if the foam pad were placed between a UWB antenna and the infant, much of the UWB energy applied would be lost in reflection or scattering. An impedance transformer pad may be configured to avoid the loss of reflection while maintaining comfort. In addition to providing a comfortable surface, the pad could be optimized to work with the UWB medical radar to optimize the energy transfer between the radar and the infant, which may be particularly important given the small size of the anatomical targets in the infant. Thus, the composition of the pad and the thickness of the pad between the radar antenna(s) and the surface of the pad may be configured to act as an impedance transformer. The UWB sensor(s), including transmitters, receivers and/or transceivers, may be integrated into an impedance transformer pad, and the impedance transformer pad may be placed beneath the infant, including on top of an existing bassinet pad/mattress or in place of such a pad.

The impedance transformer surfaces described herein may be referred to herein as impedance transformer pads or, for convenience as simply "pads", although any appropriate surface (not limited to a mattress-type pad), may be used. Such alternative embodiments, including blankets, pillows, seats, seat covers, garment, mattress covers, etc. configured as impedance transformers may also be referred to as impedance transformer pads, impedance matching pads, impedance transformers, or they may be referred to impedance transformer structures, where the structure refers to the form of the embodiment, e.g., blanket, pillow, seat, etc.

An impedance transformer pad may be used to efficiently transfer energy from one medium to another (e.g., the antenna to the infant) by minimizing reflections of the UWB energy due to impedance mismatch between the two mediums. In general, for non-conductive, non-magnetic materials, the relative dielectric constant of the two mediums (e.g., between the antenna and the subject) is the parameter of interest for this purpose.

In general, an impedance transformer pad may be formed of one or more materials (layers) interposed between the outer surface (antenna surface) of the UWB antenna and the outer surface (recumbent surface) of the pad onto which the patient will rest. These impedance transformer layers of the pad are chosen to efficiently convey UWB energy in a predetermined bandwidth between the antenna surface and the recumbent surface by controlling the thickness and the dielectric properties of the transformer layer(s).

In theory, a simple single layer impedance transformer may be fabricated from a material with a dielectric value that is the geometric mean of the two primary mediums on either side of the transformer (e.g., the antenna and the infant), and have a thickness that is an odd multiple of the fundamental wavelength of the energy. Impedance transformer pads of increasing complexity may also be used, in which the pad include multiple layers of material having different dielectric constants and specific thicknesses, as described in greater detail below.

Although a more exact determination of the thickness and dielectric composition of the impedance layer(s) of the impedance transformer pad may be calculated as taught herein and described in greater detail below, in some variations impedance transformer pads having one or more layers may be generally described as having an impedance transformer region (e.g., the region between the transmitting/receiving surface of an antenna and the recumbent surface) with a thickness between 0.4 cm and 7 cm (e.g., 0.5 cm to 5 cm, or in some variations 0.5 to 7 cm), where at least one planar layer of this impedance transformer region has a dielectric between about 5 and about 20. For example, based on the theoretical calculations and considerations described below, a typical impedance transformer pad may include an impedance transformer region formed of one or more (planar) layers of a homogenous material; the thickness of the impedance transformer region, between the outer surface of the pad (e.g., the surface contacting the infant) and the emitting/receiving surface of the antenna is typically within the range of about 0.4 cm to about 7 cm, and at least one layer of material in this region has a dielectric constant between about 5 and about 20.

Such general impedance transformer pads (having thicknesses and dielectric properties in the ranges described above) may sufficiently minimize reflection loss of the UWB signals between the UWB antenna(s) and the infant's body to substantially increase the efficiency of energy transferred between the two, and thereby the increasing the energy reflected from internal structures within the patient, increasing the strength of the received signal and the accuracy of the system. In operation, the impedance transformer pads described herein may reduce one-way reflective losses between the antenna and the subject to less than 50%.

In the context of the monitors described herein, the primary mediums in the NICU bassinet are the radar antennas and the infant; thus, the transformer material may be selected to have a relative dielectric constant that is the geometric mean of these two mediums. The impedance transformer pads may therefore be configured so that the thickness of the pad is controlled and matched to the fundamental wavelength(s) of the energy of the UWB sensor system, and the material composition of the impedance transformer pad may be controlled so that the materials chosen have a dielectric value that is within a range (e.g., the geometric mean of the antenna and the infant) of optimal values.

An impedance transformer pad may be configured to have a thickness within an optimal range based on the antenna dielectric (assuming an average patient dielectric) and the bandwidth of the UWB signal, and a dielectric (or multiple dielectrics in the case of layered pads) within an optimal range also based on the antenna properties and the bandwidth of the UWB signal. The optimal ranges of the thickness and dielectric(s) may be determined by calculation based on the principles described in greater detail below. In addition, the impedance transformer pads may also include one or more integrated UWB antenna for transmitting and/or receiving the UWB probe signals. Such components may be integrated on the back (e.g., non-patient contacting) side of the impedance transformer region of the pad, and/or integrated within the impedance transformer pads. For example, a pad may include one or more backing layers in which the antenna(s) are embedded beneath the impedance transformer region. In the discussion below, the impedance transformer region refers to the region of the pad between the outer (emitting and/or receiving) surface of the antenna(s) and the outer surface of the pad on which an infant may lie (recumbent surface).

As mentioned, the optimal thickness of the impedance transformer region of the pad may depend on the bandwidth of the UWB signal applied by the system and the dielectric properties of the impedance transformer region of the pad. The dielectric(s) of the impedance transformer region of the pad may depend on the dielectric values of the antenna and of the patient, and in the case of impedance transformer regions having multiple layers, the dielectric values of each layer may also be based on the dielectric values of the other layers of the impedance transformer region.

Figure 3A:
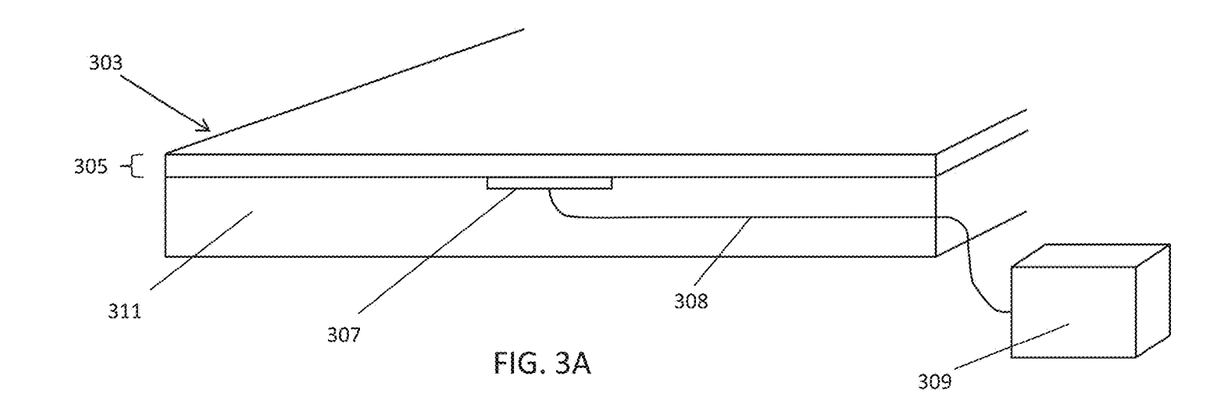
FIG. 3A is a partial sectional view through one variation of an impedance transformer pad.

FIG. 3A shows one variation of an impedance transformer pad 303 including an impedance transformer region 305 formed of a single layer. Beneath the impedance transformer layer is at least one UWB antenna(s) 307. The UWB antenna(s) may be planar antenna and may be configured as emitters, receivers and/or transceivers. The UWB antenna is coupled (e.g., via a cable 308) to a processor 309 which may form part of the UWB monitor system. The system may include the pad, antenna(s), and processor. The processor may analyze and/or output sensing data based on the UWB signals from the antenna. Additional UWB electronics may also be included. For example, of the systems and devices described herein may also include UWB electronics that are separate from or incorporated into a processor. These UWB electronics generally are configured to generating a UWB signal for transmission, and to aid in processing UWB signals (reflected signals) received the by the UWB antenna(s). UWB electronics may include signal generators, D/A and A/D converters, timing circuitry, comparators, amplifiers, filters, and the like. For example see U.S. Pat. No. 7,725,150, U.S. patent application Ser. No. 12/765,680, published as US 2010/0274145A1, and U.S. patent application Ser. No. 12/749,861, published as US 2011/0060215A1. UWB electronics may be configured to generate the UWB signal(s) for emitting from the antenna(s) and processing the received signal (reflections) to extract physiological data.

In FIG. 3A, the pad also includes a backing region 311 which may also act as a substrate on which the antenna(s) and impedance transformer surface sits. The backing region may be a foamed material, or any other appropriate material, and may have dielectric that is mismatched with the dielectric of the impedance transformer surface above it. In FIG. 3A, the impedance transformer surface may have a thickness in the range of between about 0.4 cm and 7 cm (e.g., 0.5 cm to 5 cm, or in some variations 0.5 to 7 cm). This impedance transformer surface is formed of a homogenous material having a dielectric generally between 5 and 20. In some variations this impedance transformer surface is made from a solution of silicone that has been adjusted to have the desired dielectric value by adding additives (e.g., salts, etc.). In this example, the outer impedance transformer layer is laminated directly on to the backing layer and antenna(s). For comfort, the pad may provide support, yet not be excessively hard/rigid, in order to avoid creating sores at pressure points on the body. The pad may also be easy to clean, non-toxic, hypoallergenic, and water proof. Thus, in some variations the outer impedance transforming region of the pad may be fabricated from silicone gels. As mentioned, these gels may be doped with common materials, e.g. carbon black or barium titanate, to create layers with dielectrics within the desired range (e.g., <30).

Figure 3B:
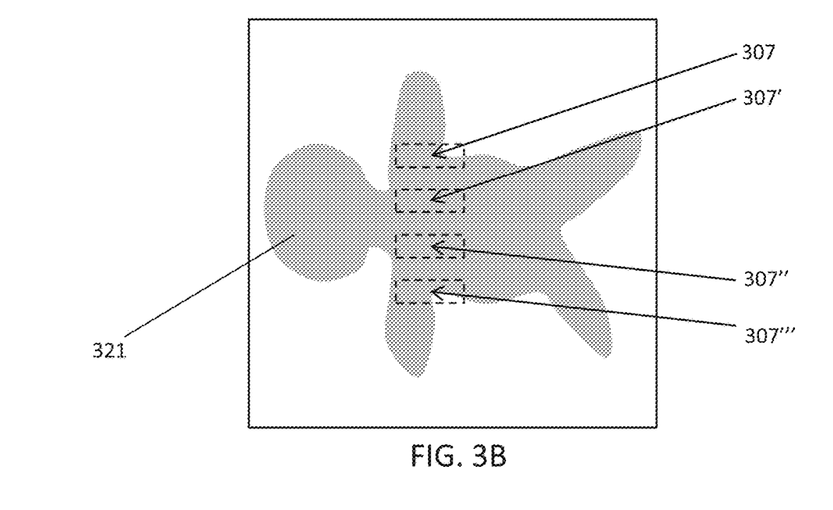
FIG. 3B shows a top view of the impedance transformer pad of FIG. 3A.

The overall shape of the pad, including the number and orientation of the UWB antennas, may be varied. FIG. 3B illustrates one variation of a UWB transformer pad for use with a UWB monitoring system that has four antenna arranged across a midline region of the pad. FIG. 3B shows a top view looking down on the outer surface of the impedance transformer region; the antenna 307, 307', 307", 307'" beneath this region are indicated by the dashed boxes. In some variations the pad may also include markings indicating the preferred positioning for a patient (e.g., infant) lying on the pad. In FIG. 3B this is illustrated by the shaded outline of the infant 321. This may be indicated on the pad visually, or the pad may simply mark (e.g., in color and/or text) the location of the antennas and/or the desired orientation of the patient. The pad may be any appropriate size. For example, the pad may be a one foot by one foot square, or it may be smaller or larger. The type and size of the UWB antenna may also be adjusted; in this example, the antennas are 2 inches long.

The range of values for the thickness and dielectric of the impedance transformer region provided above for the example shown in FIGS. 3A and 3B are general, however more precise values may be calculated given the properties of the antenna and assuming a bandwidth of the UWB signal. For example, in one variation of an impedance transformer pad having a single layer impedance transformer region of the pad, the thickness of the transmissive layer of the pad will typically be centered around about ¼ of the center frequency (e.g., the geometric mean of the bandwidth) of the applied UWB signals. A range of thicknesses may therefore be determined as optimal or appropriate from this estimate. To approximate these values, the following assumptions are made: (1) the desired transmission bandwidth is approximately 3 GHz to 6 GHz; (2) the characteristic impedance of the antenna is approximately 377 Ohm (air), and the relative dielectric constant is 1; (3) we assume that the patient's relative dielectric constant is approximately 50 (which is particularly accurate for bodies having a low fat content, such as preemies).

Assuming the bandwidth of the UWB signal is approximately 3-6 GHz, the geometric mean is approximately 4.25 GHz, which may be referred to as the center frequency ($f_c$). In this single layer example, an approximate optimized dielectric for the single layer may be based on the mean value between the dielectric of the antenna and the target (e.g., the aggregate dielectric of the infant's body). For example: for a single layer quarter wavelength pad, the relative dielectric constant of pad is the geometric mean of the dielectric of air ($\varepsilon_{air}$) and of the patient ($\varepsilon_{patient}$) or approximately 7.07 ($\varepsilon_d$). The thickness of the pad for the quarter-wavelength case is therefore equal to one quarter of the wavelength at the center frequency in the dielectric, or:

$$\text{thickness of pad} =$$

$$\lambda/4 \text{ in the dielectric} = \frac{c}{4f_c\sqrt{\varepsilon_d}} = \frac{3e10 \text{ cm/s}}{4 \times 4.24e9 \text{ c/s} \times \sqrt{7.07}} = 0.67 \text{ cm}$$

(where c is the speed of light, $f_c$ is the center frequency and $\varepsilon_d$ is the dielectric of the impedance transformer region of the pad).

Thus, in this example, a pad such as the one shown in FIGS. 3A and 3B may be made using readily commercially available air antennas ($\varepsilon_{air}$) for a bandwidth of 3-6 GHz, and therefore has a thickness of the outer impedance transformer region of approximately 0.67 cm (e.g. between 0.6 and 0.9 cm) and a dielectric value for this region of approximately 7.07 (e.g., between 5 and 9). This outer impedance transformer region may be formed of silicone that is doped with carbon black to achieve this impedance value. The pad may also include a backing region formed of foam rubber, and a plurality (e.g. 2, 3, 4, 5, 6, 7, 8, etc.) of antenna abutting the impedance transformer region so that UWB energy is directed toward the patient through the impedance transformer region. A system including such a pad may include the pad as described above (or in any of the other variations described herein) and a processor and/or additional UWB electronics communicating with the antennas in the pad; in some variations an output (e.g., one or more of audible outputs, visual outputs, electronic outputs, etc.) may also be part of the systems. The processor may include a housing, and one or more inputs (e.g., touch screens, keypads, etc.) for receiving information. In some variations the antenna may be directly coupled to UWB electronics for generating the UWB signal and/or processing the received signal reflections and extracting physiological data. For example the antenna may be integrated with some or all of the UWB electronics, or it may be connected to them, and the UWB electronics (and/or additional processor) may be positioned separately from the pad, as illustrated in FIG. 3A.

The presumed dielectric constant for the patient is based on a reasonable value for preemies. Because premature infants do not have as much body fat, their aggregate relative dielectric constant is approximately 40 to 60. As described above, based on this range of values, a single layer quarter wavelength transformer pad may be formed at least in part of a material that has a relative dielectric constant between about 5 and about 20 to efficiently couple energy from the antennas to the patient. The antenna used for the pads described herein may have a different dielectric value (e.g., other than air) and may be optimized to couple energy from the circuitry to a medium other than air, which may also reduce the physical size of the antenna. Thus, based on the antenna variation, optimal values for the dielectric constant of the impedance transformer pads could be somewhat lower or higher, and may be within the range, for example, of about 5 to about 25.

A single layer quarter wavelength impedance transformer pad may be particularly useful with narrowband signals, though its performance may degrade as the bandwidth of the signal increases, as is the case with UWB radar. To compensate for this, multilayer transformers pads may be used, and may be better suited to minimize reflections across the desired portion of the spectrum. Exemplary multilayer transformers pads may include a 2 layer "quarter-quarter" transformer pad and a 3 layer "quarter-half-quarter" transformer pad, where the quarter and half references are with respect to the estimated wavelength of the center frequency of the UWB monitor. Pads having more than three layers for the impedance transformer region are also contemplated.

For example, three exemplary variations of impedance transformer pads are: quarter, quarter-quarter, and quarter-half-quarter variations. The quarter-quarter is variation may provide improved bandwidth and can be fabricated from materials with dielectrics between those of the characteristic impedance of the antennas and the dielectric of the patient. The quarter-half-quarter may use a material for the half layer that has a dielectric significantly above either of the other two (quarter layers) for an improvement in bandwidth over the quarter and quarter-quarter layer variations. Numerous other topologies, including more than three layers, are possible. Typically, however, the greater the number of layers, the larger associated materials cost and manufacturing complexity; additional layers may, however, provide a modest improvement in performance.

As an example, a three layer transformer ("quarter-half-quarter" transformer pad) may provide good performance over a 100% bandwidth case, e.g. 3 GHz to 6 GHz. Similarly, other transformer pad structures, including multiple layers, can be employed to enhance energy transfer.

Figure 5:
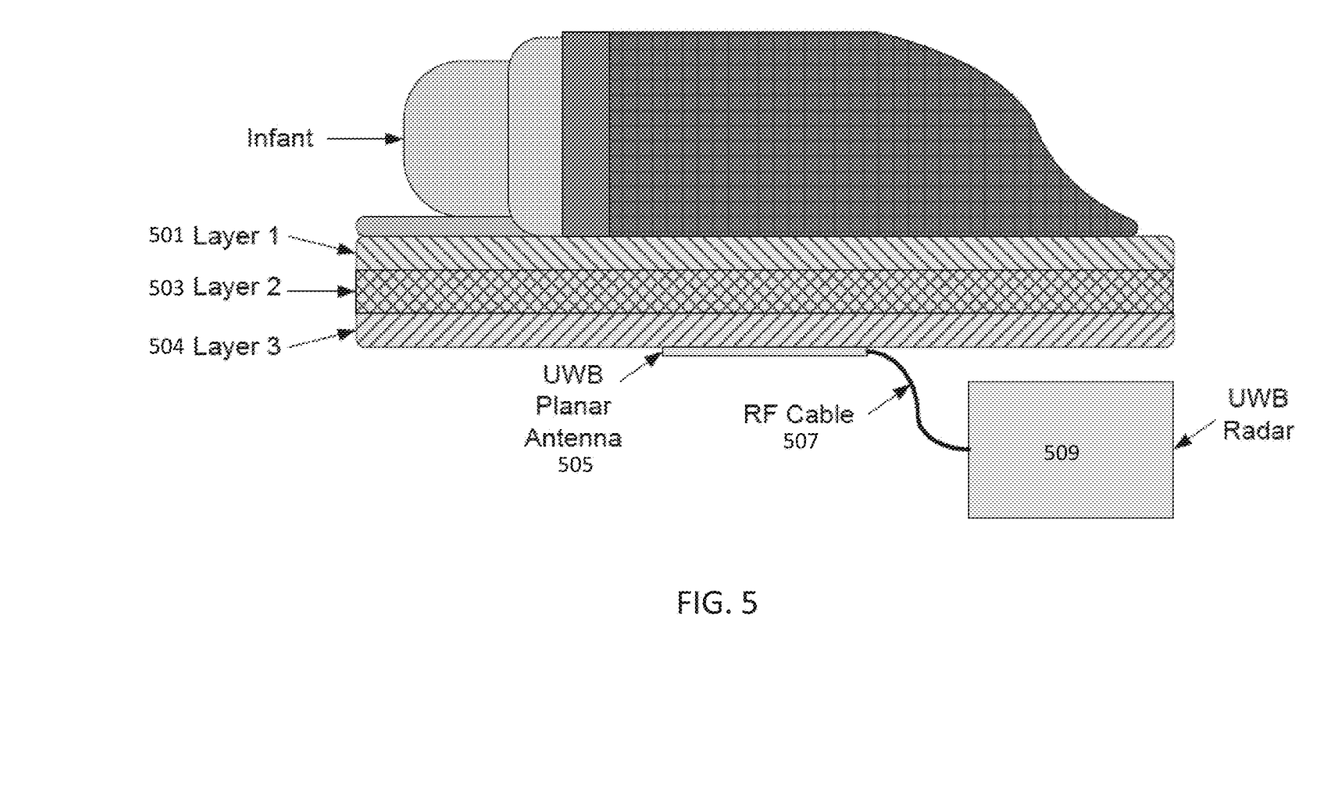
FIG. 5 shows another variation of a UWB monitoring system for an infant, including an impedance matching pad having three layers in the impedance matching region.

FIG. 5 illustrates one variations of an impedance transformer pad that has an impedance transformer region formed of three layers; a ¼ wavelength layer, a ½ wavelength layer, and ¼ wavelength layer. By having multiple layers, it may be possible to expand the bandwidth over which the transformer pad effectively moves energy. Each layer is designated by the fraction of the center frequency ($f_c$), e.g., ¼ wavelength, ½ wavelength, etc. as a function of the dielectric of the layer.

Figure 2:
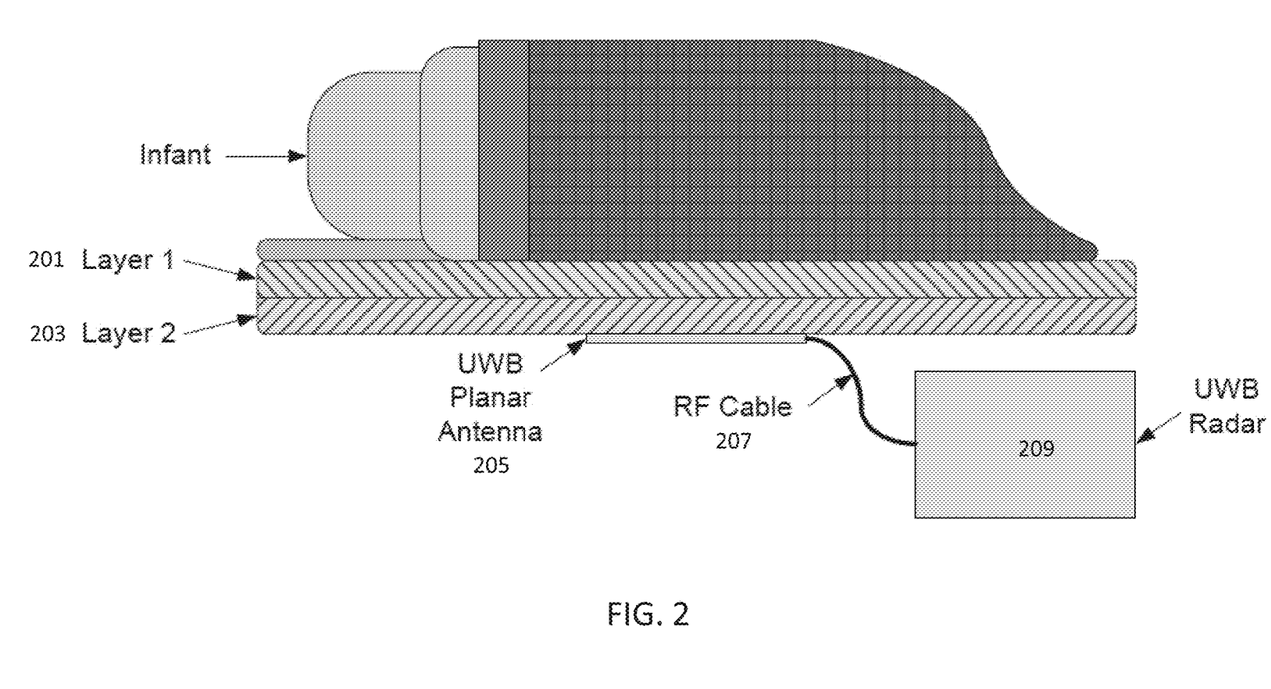
FIG. 2 shows one variation of a UWB monitoring system for an infant, including an impedance matching pad.

In FIG. 5, a UWB system includes an impedance transforming pad having three layers: a quarter (¼ wavelength) layer 501, a half (½ wavelength) layer 503, and another quarter (¼ wavelength) layer 504. Thus, this variation may be referred to as a quarter-half-quarter wavelength impedance transformer pad, and includes at least one integrated UWB antenna 505. As illustrated in FIG. 2, the antenna may be a UWB planar antenna 505, and may communicate with a UWB processor 509 (e.g., via RF cable 507 or other means, including wirelessly). As mentioned above, additional UWB electronics for generating the UWB signal(s) for transmission, receiving the UWB signal reflections, and for processing the reflections to extract the desired physiological data may be included as part of the processor, or separately. Further these features may be integrated with the antenna or separate from the antenna and connected as mentioned above.

In general, pads of this variation may also fall into the same range of values for the thickness and dielectric values of the impedance transformer region described generally above, however each layer may have its own characteristic dielectric value, and specific thickness. The overall thickness may typically be between 0.4 cm and 7 cm (the aggregate thickness of all layers of the impedance transformer region), and at least one layer of the impedance transformer region may have a dielectric value between about 5 and about 20.

For example, one variation of an impedance transformer pad having a three layer quarter-half-quarter impedance transformer region may be formed so that each layer has the following dielectric and thickness values, which may be estimated. Referring to the arrangement of FIG. 5 and making the same assumptions mentioned above (e.g., an antenna having a $\varepsilon_{air}$ of 1, a bandwidth of 3-6 GHz and a patient having a $\varepsilon_{body}$ of 50), the values may be calculated as illustrated below.

The half wavelength layer (layer 2) 503 may be formed of a material that is selected for cost and/or ease of manufacturing. In this example, assume that the dielectric ($\varepsilon_{d2}$) is 5. Other materials, having other dielectric values (ranging from 1 to >50) may be used. Based on this value, the thickness may be calculated as:

Thickness of layer 2 =

$$\lambda/2 \text{ in the dielectric} = \frac{c}{2f_c\sqrt{\varepsilon_{d2}}} = \frac{3e10 \text{ cm/s}}{2 \times 4.24e9 \text{ c/s} \times \sqrt{5}} = 1.58 \text{ cm}$$

Similarly layer 3, which is the layer of the impedance transformer region closes to the antenna has a relative dielectric constant that is the geometric mean of air and layer 2, or approximately 2.24 (e.g., the square root of $\varepsilon_{air}$ and $\varepsilon_{d2}$). Based on this dielectric, the thickness of this layer is:

Thickness of layer 3 =

$$\lambda/4 \text{ in the dielectric} = \frac{c}{4f_c\sqrt{\varepsilon_{d3}}} = \frac{3e10 \text{ cm/s}}{4 \times 4.24e9 \text{ c/s} \times \sqrt{2.24}} = 2.64 \text{ cm}$$

Layer 1 is the remaining layer closest to the outer surface of the impedance transformer region, closest to the recumbent surface. The relative dielectric constant of layer 1 ($\varepsilon_{d1}$) is a function of dielectrics of the antennas, layer 3, and patient. It can be calculated using the equation:

$$\sqrt{\frac{\varepsilon_3^2 * \varepsilon_{body}}{\varepsilon_a}}$$

where:
$\varepsilon_a$=relative dielectric constant associated with the antenna(s),
$\varepsilon_3$=relative dielectric constant of layer 3, and
$\varepsilon_{body}$=relative dielectric constant of patient's body Thus, the relative dielectric constant of layer 1 =

$$\sqrt{\frac{\varepsilon_3^2 * \varepsilon_{body}}{\varepsilon_a}} = \sqrt{\frac{2.24^2 * 50}{1}} = 15.84.$$

based on this dielectric, the thickness of layer 1 can be calculated as described above as:

Thickness of layer 1 =

$$\lambda/4 \text{ in the dielectric} = \frac{c}{4f_c\sqrt{\varepsilon_{d1}}} = \frac{3e10 \text{ cm/s}}{4 \times 4.24e9 \text{ c/s} \times \sqrt{15.84}} = 0.44 \text{ cm}$$

Thus, the thickness of the impedance transformer region is the aggregate thickness of all three layers (0.44 cm+1.58 cm+2.64 cm), 4.66 cm, and the dielectric constants are: 15.84, 2.24 and 5. Pads such as those illustrated above having three layers (e.g., configured as Quarter-Half-Quarter pads) may be particularly useful, as the bandwidth may be better than single or double layer variations.

Figure 4A:
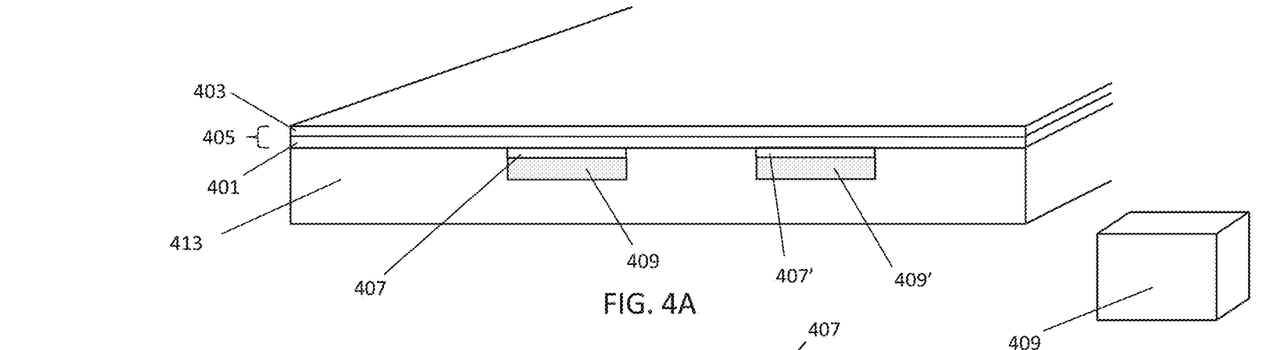
FIG. 4A is a partial sectional view through another variation of an impedance transformer pad.
Figure 4B:
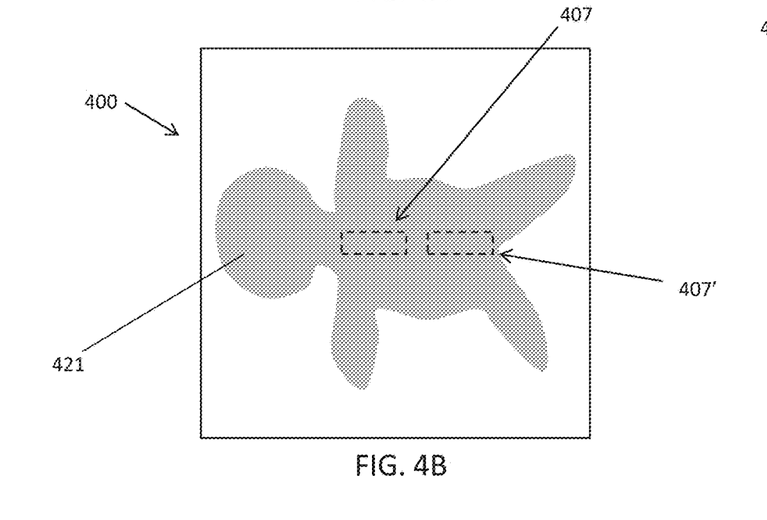
FIG. 4B is a top view of the impedance transformer pad of FIG. 4A.

FIGS. 4A and 4B illustrate a double-layer variation of an impedance transformer pad of a UWB system, configured as a quarter-quarter transformer pad. In this example, the pad includes an impedance transformer region 405 formed of a first layer 403 and a second layer 401. In this example, the antennas 407, 407' abut the second layer 401, and includes signal handling components 409, 409', which may include on-board circuitry (e.g., signal processing) and/or communications circuitry for passing the signal to other portions of the UWB system 409, which may include an off-pad processor and/or UWB electronics. In some variations, the processor and any additional UWB electronics may be integrated into the pad.

FIG. 4B shows a top view of another variation of an impedance transformer pad 400, similar to the variation shown in FIG. 3B. In this example, the positions of two antenna are indicated by the dashed boxes 404, 407' beneath the outer surface of the pad. As mentioned, any appropriate number and positioning of antennas allowing the UWB signal to reach an infant lying on the pad may be used. Antennas which may be used as part of an impedance transformer pad include planar structures (antenna), which may minimize discomfort and are typically designed to couple energy from the electronic circuitry to air.

In any of the variations of the impedance transformer pad having impedance transformer regions formed of multiple layers, the various layers may be laminated together. Thus, for example, single, double, triple, or more layers may be used, as indicated. In addition, one or more additional backing layers (e.g., foam backing layers) may be laminated or otherwise affixed to the impedance transformer region.

In all of the variations illustrated above, the impedance transformer region is formed as a planar layer extending across the entire surface of the pad. In some variations the impedance transformer region extends only over a sub-region of the surface of the pad, which may be limited to just the region above the antenna and between the antenna transmission/receiving surface and the upper (recumbent) surface of the pad. In some variations the impedance transformer region may be slightly larger than the underlying antenna surface. Multiple such impedance transformer regions ("islands") may extend across the surface of the pad over top of each antenna; these discrete impedance transformer regions maybe surrounded by the same support layer material (e.g., foam rubber, etc.) as beneath the impedance transformer region. Such variations may be particularly useful where multiple types of antennas having different properties (e.g., different dielectrics) are used. In this variation, the different impedance transformer regions may have a different number of layers or may have different characteristic thicknesses and/or dielectrics.

Returning now to FIG. 2, another variation of an impedance transformer pad configured as a quarter-quarter impedance transformer pad with an integrated UWB antenna is illustrated. In this example, the impedance transformer pad includes two layers (first layer 201 and a second layer 202) and an integrated planar UWB antenna 205 which is attached to the underside of the impedance transformer pad. The UWB antenna is shown connected via RF cable 207 to a UWB processor 209, which may be located outside of the bassinet. Additional UWB electronics (not shown) may also be included (as part of or in addition to the UWB processor) for generating the signal(s), conditioning the received signal(s) and/or extracting information from the received signal(s). Alternatively, in some variations, the processor 209 and other UWB components (e.g., electronics) may be located within the bassinet or may be coupled wirelessly to the antenna 205. In some variations, the processor controls the transmission and reception of UWB signals and may provided signal processing and analysis of the patient's (e.g., infant's) vitals. Outputs, including alarms, storage of signals (including alarms, etc.), and transmission of data from the UWB system may also be coordinated and controlled by the processor.

The impedance transformer pads described herein may address problems and inefficiencies present in other UWB senor systems, particularly those used for recumbent patients. As mentioned above, "mattress" UWB sensors for monitoring the health of an individual in a bed or chair have been described, but have not been optimized to improve radar performance. Optimization would not be possible when UWB systems are used with standard mattress materials. For example, foam rubbers used in most mattresses are made from styrene-butadiene or polyurethane, which have relative dielectric constants in the range of 2 to 4 prior to being converted into foam, outside of the optimal dielectric range. To create foam rubber, the base rubber compounds have gas injected into them during manufacturing to decrease hardness and improve comfort as well as increase insulating properties, and the introduction of gas reduces the dielectric constant of these materials proportionally to the percentage of gas by volume used in the product. Also, gas bubbles cause scattering, reducing the performance of the radar. Both the miss-match of the extremely low relative dielectric constants and scattering by gas bubbles make traditional foam rubber mattress materials unsuitable for use in an impedance transformer as described herein. Further, the thicknesses of mattresses are much larger than the range of thicknesses described herein for optimal configuration of an impedance transformer pad.

Signal Processing

Data from the UWB medical radar system may be processed to provide appropriate outputs, including cardiac wall motion waveforms or indicators, cardiac rate waveforms or indicators, and respiratory waveforms or indicators as well as refined data derived from these basic data types. Programmable alarms may be set by caregivers to alert them of changes to the infant's condition. The resulting data could be displayed on a local monitor or a centralized monitor. With connection to the hospital network, the data could be accessed by healthcare professionals remotely.

In addition to detection of basic vital signs, including cardiac and respiratory activity, the UWB sensor systems described herein may be programmed to detect other motions, including heads turns or limb movement, and could be configured so that the absence of age-appropriate motion over a pre-defined period of time triggers alarms, prompting caregivers to check on the infant. For example, in some variation the processor may receive one or more inputs that may help it to monitor the infant. For example, the processor may receive the infant's age and use this information to appropriate toggle alerts or analysis information. For example, the amount of motion typically observed in premature babies is a function of gestational age at the time of birth. For example, a baby born at 28 weeks or less does not move much, with motion limited to fist clinches or limb flexes. Between 29 and 32 weeks of gestation, motion is jerky and can include head turns. At 35 weeks, the baby is capable of a variety of motions, including tucking into the fetal position. In addition, other sensors, such as temperature (e.g., infrared) sensors, pressure sensors, or the like, could be integrated to provide enhanced monitoring capabilities.

In general, the UWB signals generated and proceed to determine vital properties (e.g., heart rate, body movements, and the like) may be handled as previously described, for example, in U.S. Pat. No. 7,725,150, U.S. patent application Ser. No. 12/765,680, published as US 2010/0274145A1, and U.S. patent application Ser. No. 12/749,861, published as US 2011/0060215A1.

The system may further be configured to integrate with one or more other hospital monitors, records, or hospital control systems. Thus, these monitors may interface with existing infant monitoring systems. For example, the processor may allow communication/interface with other monitoring or hospital patient care systems.

In addition, the systems and devices described herein may include automatic on/off or other power management functions, which may also be used to toggle alerts and data collection. For example, the UWB sensors/impedance transformer pads described herein may determine when the patient (e.g., infant) is laying on the recumbent surface (e.g., impedance transformer pad). Since these devices efficiently transfer energy between the UWB antenna and patient, the voltage standing wave ratio (VSWR) will reflect when the patient is not present on the pad. This is relatively simple to detect in the sensor and can be used as a way to tell when a patient is present, allowing the radar to go into a "sleep" mode when the patient is gone. In sleep mode, the radar may occasionally "wake up" to test for the presence of the patient and when detected, resume full operation. The system may also be set up to trigger an alarm if the VSWR ratio indicates that the patient has moved off of the impedance transformer pad.

In general, the impedance transformer pads described herein may be adapted for comfort, as the infant may be placed directly on them. Furthermore, these pads may be well adapted for use as a sleeping surface, and particularly for an infant sleeping surface. For example, the impedance transformer pads may be flexible, pliable, soft, and/or resilient. The pad may be configured to be easily removed (and may therefore contain coupling/uncoupling features whereby the integrated UWB antenna components in the impedance transformer pads may be uncoupled and reconnected to the rest of the UWB monitoring system (including one or more processors, displays, etc.). The impedance transformer pads may also be configured so that it can be easily and safely washed or laundered and/or sterilized. Thus, the impedance transformer pad may include a waterproof or water resistant outer coating, and the antenna components may be protected from corrosion or degradation by washing, or by contamination from blood, urine, or the like.

Any of the impedance transformer pads described above may also include one or more indicators, including markings, illuminated regions (e.g., LEDs, etc.) indicating the optimal placement or positioning of the subject on the pad, and/or the orientation of the pad on or relative to the bassinet, bed, seat, etc. For example, the impedance transformer pad may include a color-coated or otherwise labeled region indicating how the infant is to be oriented when laying on the pad, such as where to optimally position the head and torso.

Although the variations of the UWB monitoring systems described above are illustrated in the context of infant/NICU embodiments, these systems and devices may be used and/or adapted for use by non-infant (including adult or veterinarian) use. For example, a impedance transformer pad may be used on top of an adult-sized mattress for use with one or more adult patients, including gerontological or hospital use.

Other variations of the devices and systems described herein include, in particular, garments, seats, and/or blankets configured as impedance transformer pads for use with UWB monitoring systems. Such impedance transformer pads may be configured with integrated antennas and the appropriate thickness and dielectric properties. For example, an impedance transformer pads may be configured as part of car seat that may be used over an existing car seat and may optimally provide feedback to a mobile UWB monitoring systems. In other variations, a blanket or bedcovering may be configured as an impedance transformer pad, which may be applied over a patient, or beneath them as a mattress pad or the like.

In particular, variations of the systems described here may be used for home (rather than just NICU) monitoring. For example, parents, particularly those of infants with medical problems, are often concerned about the undetected onset of emergent medical problems when their child is asleep. It may therefore be desirable to use the devices described herein for active baby monitoring. Currently available baby monitors include traditional audio and video monitors as well as crib pads with motion sensors capable of detecting motion and respiration. The systems described above could be used to provide a monitoring able to detect cardiac activity and other vital signs, including gross body motion. Simplified variations of the system may be adapted for home use, including systems limited to one or two radar components, such as a single transceiver, a separate transmitter and receiver, or two transceivers. These systems may include an impedance transformer pad as described above, or may be configured to mount or hang from the child's crib. A communications link may be used to transmit infant data to a small receiving station that the parents could carry with them or place nearby.

While the foregoing has been with reference to particular embodiments of the invention, it will be appreciated by those skilled in the art that changes in these embodiments may be made without departing from the principles and spirit of the invention, the scope of which is defined by the appended claims. The intention(s) described herein are intended to cover all modifications, equivalents, and alternatives falling within the spirit and scope of the invention as defined by the appended claims. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of monitoring a human using an electromagnetic energy radar system including an impedance transformer pad of a vehicle seat, the method comprising:
   positioning the human adjacent to the impedance transformer pad having a plurality of adjacent planar layers wherein at least two layers of the plurality of adjacent planar layers have a different dielectric, and wherein the thickness of each layer of the plurality of adjacent planar layers is approximately one quarter or one half of the wavelength of the center frequency of the bandwidth in the dielectric of that layer;
   emitting a signal from an antenna beneath the impedance transformer pad, wherein the signal passes from the antenna, through an impedance transformer region of the impedance transformer pad and into the human, further wherein the impedance transformer region is arranged so that the dielectric constants of the adjacent planar layers increase towards the human and are between about 5 and about 20,
   wherein the impedance transformer pad reduces the impedance mismatch between the antenna and the human to reduce reflective loss of energy from the signal;
   receiving a reflected signal from the human using the antenna, wherein the reflected signal is based on the signal emitted from the antenna; and
   analyzing, with the electromagnetic energy radar system, the reflected signal to monitor the human.

2. The method of claim 1, wherein emitting the signal comprises passing the signal through the impedance transformer region wherein the impedance transformer region has a single homogenous planar layer having a dielectric that is a geometric mean of the dielectric of the antenna and the dielectric of the human.

3. The method of claim 1, wherein emitting the signal comprises passing the signal through the impedance transformer region wherein the impedance transformer region has a thickness between about 0.4 cm and about 7 cm.

4. The method of claim 1, wherein emitting comprises emitting the signal from the antenna to the human through the impedance transformer region without passing through the air.

5. The method of claim 1 wherein the electromagnetic energy radar system comprises an ultra wideband (UWB) radar system, the signal comprises a UWB signal, and the antenna comprises a UWB antenna.

6. The method of claim 1 wherein the human comprises a child.

7. A vehicle seat for monitoring a human using an ultra wideband (UWB) radar system comprising:
   a seating structure;
   a UWB antenna;
   an impedance transformer pad coupled to the UWB antenna, the impedance transformer pad having a plurality of adjacent planar layers wherein at least two layers of the plurality of adjacent planar layers have a different dielectric, wherein the impedance transformer pad is configured to be received by the seating structure, wherein the impedance transformer pad is configured for emitting a UWB signal from the UWB antenna, wherein the signal passes from the antenna, through an impedance transformer region of the impedance transformer pad and into the human, further wherein the impedance transformer region is arranged so that the dielectric constants of the adjacent planar layers increase towards the human and are between about 5 and about 20, wherein the impedance transformer pad reduces the impedance mismatch between the antenna and the human to reduce reflective loss of energy from the signal, wherein the UWB antenna is configured to receive a reflected signal, wherein the reflected signal is based on the signal emitted from the UWB antenna, wherein the impedance transformer pad is configured to enhance energy of the reflected signal to the UWB antenna.

8. The vehicle seat of claim 7, wherein emitting the UWB signal comprises passing the signal through the impedance transformer region wherein the impedance transformer region has a single homogenous planar layer having a dielectric that is a geometric mean of the dielectric of the antenna and the dielectric of the human.

9. The vehicle seat of claim 7, wherein emitting the UWB signal comprises passing the signal through the impedance transformer region wherein the impedance transformer region has a thickness between about 0.4 cm and about 7 cm.

10. The vehicle seat of claim 7, wherein emitting comprises emitting the UWB signal from the antenna to the human through the impedance transformer region without passing through the air.

11. The vehicle seat of claim 7 wherein the human comprises a child.

12. A method of monitoring a human using an ultra wideband (UWB) radar system including an impedance transformer pad, the method comprising:

positioning the human adjacent to the impedance transformer pad having a plurality of adjacent planar layers wherein at least two layers of the plurality of adjacent planar layers have a different dielectric, and wherein the thickness of at least one layer of the plurality of adjacent planar layers is approximately one quarter or one half of the wavelength of the center frequency of the bandwidth in the dielectric of that layer and at least one layer of the plurality of adjacent planar layers has a different thickness;

emitting a UWB signal from a UWB antenna beneath the impedance transformer pad, wherein the signal passes from the antenna, through an impedance transformer region of the impedance transformer pad and into the human, further wherein the dielectric constants of the planar layers are between about 5 and about 20, and wherein the impedance transformer pad reduces the impedance mismatch between the antenna and the human to reduce reflective loss of energy from the signal;

receiving a reflected UWB signal from the human using the UWB antenna, wherein the reflected signal is based on the UWB signal emitted from the UWB antenna; and analyzing the reflected UWB signal to monitor the human.

13. The method of claim 12, wherein emitting the UWB signal comprises passing the signal through the impedance transformer region wherein the impedance transformer region has a single homogenous planar layer having a dielectric that is a geometric mean of the dielectric of the antenna and the dielectric of the human.

14. The method of claim 12, wherein emitting the UWB signal comprises passing the signal through the impedance transformer region wherein the impedance transformer region has a thickness between about 0.4 cm and about 7 cm.

15. The method of claim 12, wherein placing comprises placing the human atop the impedance transformer pad within a Neonatal Intensive Care Unit (NICU) bassinet.

16. The method of claim 12, wherein emitting comprises emitting the UWB signal from the antenna to the human through the impedance transformer region without passing through the air.

17. The method of claim 12 wherein the impedance transformer pad is configured to operate with a vehicle seat.

18. The method of claim 12 wherein the impedance transformer pad is configured to operate on a table, a platform, a mattress, a cushion, a blanket, a bed, a chair, a seat or a pillow.

19. The method of claim 12 wherein the human comprises a child.

* * * * *